United States Patent
de Paoli Ambrosi (10) Patent No.: US 9,511,112 B2
(45) Date of Patent: Dec. 6, 2016

(54) ANTIBACTERIAL COMPOSITION FOR TOPICAL USE

(71) Applicant: GENERAL TOPICS S.r.l., San Felice del Benaco (BS) (IT)

(72) Inventor: Gianfranco de Paoli Ambrosi, Salò (IT)

(73) Assignee: GENERAL TOPICS S.R.L., San Felice del Benaco (BS) (IT)

( * ) Notice: Subject to any disclaimer, the term of this patent is extended or adjusted under 35 U.S.C. 154(b) by 0 days.

(21) Appl. No.: 14/418,682

(22) PCT Filed: Jul. 29, 2013

(86) PCT No.: PCT/IB2013/056199
§ 371 (c)(1),
(2) Date: Jan. 30, 2015

(87) PCT Pub. No.: WO2014/020516
PCT Pub. Date: Feb. 6, 2014

(65) Prior Publication Data
US 2015/0209405 A1    Jul. 30, 2015

(30) Foreign Application Priority Data
Aug. 1, 2012 (IT) .............................. BS2012A0126

(51) Int. Cl.
| | | |
|---|---|---|
| *A61K 38/10* | (2006.01) | |
| *A61K 8/64* | (2006.01) | |
| *A61K 8/37* | (2006.01) | |
| *A61K 45/06* | (2006.01) | |
| *A61K 31/60* | (2006.01) | |
| *A61Q 17/00* | (2006.01) | |
| *A61K 31/232* | (2006.01) | |
| *A61K 33/30* | (2006.01) | |
| *A61K 8/27* | (2006.01) | |
| *A61K 31/7056* | (2006.01) | |
| *A61K 8/60* | (2006.01) | |
| *A61K 31/7048* | (2006.01) | |
| *A61K 31/225* | (2006.01) | |
| *A61K 8/368* | (2006.01) | |
| *A61K 38/17* | (2006.01) | |
| *A61K 9/00* | (2006.01) | |
| *A61K 31/231* | (2006.01) | |
| *A61K 47/10* | (2006.01) | |
| *A61K 47/14* | (2006.01) | |
| *A61K 47/32* | (2006.01) | |
| *A61K 8/362* | (2006.01) | |
| *A61Q 11/00* | (2006.01) | |

(52) U.S. Cl.
CPC ................ *A61K 38/10* (2013.01); *A61K 8/27* (2013.01); *A61K 8/362* (2013.01); *A61K 8/368* (2013.01); *A61K 8/37* (2013.01); *A61K 8/602* (2013.01); *A61K 8/64* (2013.01); *A61K 9/0014* (2013.01); *A61K 31/225* (2013.01); *A61K 31/231* (2013.01); *A61K 31/232* (2013.01); *A61K 31/60* (2013.01); *A61K 31/7048* (2013.01); *A61K 31/7056* (2013.01); *A61K 33/30* (2013.01); *A61K 38/1751* (2013.01); *A61K 45/06* (2013.01); *A61K 47/10* (2013.01); *A61K 47/14* (2013.01); *A61K 47/32* (2013.01); *A61Q 11/00* (2013.01); *A61Q 17/00* (2013.01); *A61K 2800/5922* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 7,169,811 B2 * | 1/2007 | de Paoli Ambrosi | .... A61K 8/37 514/506 |
| 2005/0148495 A1 | 7/2005 | Lambert et al. | |
| 2007/0207112 A1* | 9/2007 | Gormley | ................ A61K 8/368 424/70.14 |

FOREIGN PATENT DOCUMENTS

| | | |
|---|---|---|
| EP | 1269991 A2 | 1/2003 |
| WO | 02079408 A2 | 10/2002 |
| WO | 2007066371 A1 | 6/2007 |

OTHER PUBLICATIONS

Charakida A et al: "Double-blind, randomized, placebo-controlled study of a lotion containing triethyl citrate and ethyl linoleate in the treatment of acne vulgaris.", The British Journal of Dermatology Sep. 2007 (Sep. 2007), vol. 157, No. 3, Sep. 2007, pp. 569-574, XP002692907, ISSN: 0007-0963 See abstract , and p. 573, conclusive paragraph: triethyl citrate and ethyl linoleate are effective for treating acne and seborrhea.

Database EMBASE [Online] Elsevier Science Publishers, Amsterdam, NL; 2011, Placek W et al: "Topical treatment of acne", XP002692908, Database accession No. EMB-2011695323 Triethyl citrate is one of the few substances affecting all mechanisms involved in the aetiopathogenesis of acne & Placek W et al: "Topical treatment of acne" , Przeglad Dermatologiczny 2011 Wydawnictwo Czelej Sp. Z.O.O. Pol , vol. 98, No. 5, 2011 , pp. 442-448, ISSN : 0033-2526.

* cited by examiner

*Primary Examiner* — Amber D Steele
*Assistant Examiner* — Schuyler Milton
(74) *Attorney, Agent, or Firm* — Volpe and Koenig, P.C.

(57) ABSTRACT

The present invention relates to an antibacterial composition, preferably for topical use, comprising triethyl citrate and a peptide consisting of 15 amino acids of sequence FAKALKALLKALKAL-NH2 (SEQ ID NO: 1), wherein F is phenylalanine, A is alanine, K is lysine and L is leucine, particularly for the treatment of acne, suppurative or non-suppurative hidradenitis, atopic dermatitis characterized by colonization by *Staphylococcus Aureus*, impetigo, interdigital infections, folliculitis, boils, post-traumatic infections, and burned skin infections.

17 Claims, 5 Drawing Sheets

ANTIBACTERIAL COMPOSITION FOR TOPICAL USE

CROSS REFERENCE TO RELATED APPLICATIONS

This application is a 35 USC §371 national stage application of PCT/IB2013/056199, which was filed Jul. 29, 2013 and claimed priority to Italian Patent Application No. BS2012A000126, filed Aug. 1, 2012.

FIELD OF THE INVENTION

The present invention relates to an antibacterial composition for topical use, and particularly to a composition of the above type intended to counteract bacterial colonization and apt for use on both damaged and non-damaged skin as well as on mucous membranes, including oral mucosa.

STATE OF THE ART

The use of either bacteriostatic or bactericidal antibiotics is known to counteract bacterial infections to which humans are subjected, which may be different in nature.

Although antibiotics are advantageous, they are not free from drawbacks because they generally involve side effects including imbalance of the bacterial flora of the skin, occurrence of allergic reactions, toxic effects in various districts of the organism, as well as intolerance in case of interaction with other substances, especially other drugs.

Furthermore, the overuse of antibiotics may result in the occurrence of an antibiotic resistance which can be acquired by the pathogenic agent, thus rendering ineffective the antibiotic therapy which nevertheless should be continued for a medium to long period in order to be successful.

In any case, the abuse of antibiotics may pose serious consequences to human organism which may even lead to death.

In order to overcome the above drawbacks, alternative approaches to antibiotics have been investigated, particularly for the treatment of skin and mucous membranes suffering from diseases such as acne, which approaches showed the antimicrobial activity of a peptide as described in document US 2007/0207112.

Particularly, the above document describes that the bacterial colonization in a patient with acne can be controlled by a peptide consisting of a sequence of 15 amino acids comprising phenylalanine (F), alanine (A), lysine (K) and leucine (L) in the order FAKALKALLKALKAL-NH2 (SEQ ID. NO: 1).

This peptide is derived from a biocidal protein defined as a "bacterial/permeability-increasing protein", generally referred to as BPI, which forms part of the innate immune system as described in document US 2005/0148495.

Although the BPI(s) show biocidal activity, however, they are known to be active mainly against Gram-negative bacteria.

SUMMARY OF THE INVENTION

Accordingly, the technical problem underlying the present invention is to provide an antibacterial composition capable of overcoming the drawbacks mentioned with reference to the prior art, particularly a composition having a high effectiveness and suitable for the treatment of a variety of skin diseases while not showing any side effect or otherwise undesired effect.

According to the invention, the above-mentioned problem is solved by an antibacterial composition preferably intended for topical use, apt to be used on both damaged and non-damaged skin, mucous membranes including oral mucosa, and skin appendages, and comprising triethyl citrate and a peptide consisting of 15 amino acids of sequence FAKALKALLKALKAL-NH2 (SEQ ID NO: 1), in which F is phenylalanine, A is alanine, K is lysine and L is leucine.

Unexpectedly, the composition according to the invention showed a synergistic activity, and particularly, it showed a high microbiocidal action and a high ability to inhibit bacterial colonization by both Gram-positive and Gram-negative, aerobic and anaerobic bacteria including, by way of a non-limiting example: *Staphylococcus Aureus, Propionibacterium acne, Pseudomonas aeruginosa, Streptococcus pyogenes, Staphylococcus epidermis*, while being simultaneously able to inhibit the degradation of skin triglyceride molecules induced by enzymes released by Gram-positive and Gram-negative, aerobic and anaerobic bacteria, thereby controlling the genesis of inflammatory process determined by the free fatty acids resulting from triglyceride hydrolysis.

Therefore, according to the invention, the present composition is apt to counteract bacterial infections of skin, mucous membranes and skin appendages, and it is apt to the treatment of pathologies in which a skin infection causes, or contributes to cause, detectable lesions on the skin, such as for example in acne, suppurative or non-suppurative hidradenitis, atopic dermatitis characterized by colonization by *Staphylococcus Aureus*, impetigo, interdigital infections, folliculitis, boils, post-traumatic infections, and burned skin infections.

Preferably, the composition according to the invention comprises triethyl citrate at a concentration in the range from 0.05 w/w % to 99.9 w/w %, more preferably from 0.5 w/w % to 45 w/w %, still more preferably from 2.5 w/w % to 15 w/w %.

Preferably, the composition according to the invention comprises the above said peptide at a concentration in the range from 0.002 w/w % to 0.5 w/w %, more preferably from 0.010 w/w % to 0.35 w/w %, still more preferably from 0.010 w/w % to 0.125 w/w %.

According to further embodiments of the invention, the present composition may also comprise one or more synergistic agents selected from essential fatty acids including salts and esters thereof, salicylic acid including salts and esters thereof, zinc and derivatives thereof, azelaic acid, octadecenedioic acid, and antibiotics.

Preferably, one or more synergistic agents belonging to the group consisting of essential fatty acids and salts and esters thereof are included in the present composition at a concentration in the range from 0.01% to 50 w/w %, more preferably from 0.5 w/w % to 15 w/w %, and advantageously, linoleic acid, linolenic acid and oleic acid are more preferred.

Preferably, one or more synergistic agents belonging to the group consisting of salicylic acid and salts and esters thereof are included in the present composition at a concentration in the range from 0.2 w/w % to 15 w/w %, more preferably from 0.5 w/w % to 2 w/w %.

Preferably one or more synergistic agents belonging to the group consisting of zinc and derivatives thereof are included in the present composition in a concentration from 0.2 w/w % to 5 w/w %, more preferably from 0.5 w/w % to 2 w/w %, and advantageously zinc oxide, zinc sulfate, zinc pyrithione, zinc mandelate, zinc acetate, zinc glycolate, zinc salicylate, zinc lactate, zinc pyruvate, are more preferred.

Preferably, one or more synergistic agents belonging to the group consisting of azelaic acid and octadecenedioic acid are included in the present composition at a concentration in the range from 1 w/w % to 65 w/w %, more preferably from 2 w/w % to 15 w/w %.

Preferably, one or more synergistic agents belonging to the group consisting of antibiotics are included in the present composition at a concentration in the range from 0.1 w/w % to 5 w/w %, more preferably from 0.5 w/w % to 2 w/w %, and advantageously, isoxacillins including oxacillin, cloxacicillin, dicloxacillin, nafcillin and flucloxacillin; aminopenicillins including ampicillin and amoxicillin; carboxypenicillins including carbenicillin and ticarcillin; ureidopenicillins including mezlocillin, piperacillin, azlocillin and apalcillin; as well as benzylpenicillin, sulfadimidine, sulfamerazine, streptomycin, sulfadiazine, chlortetracycline, chloramphenicol, neomycin, oxytetracycline, penicillin G procaine, erythromycin, benzathine penicillin, spiramycin, tetracycline, thiamphenicol, vancomycin, phenoxymethylpenicillin, colistin, demeclocycline, virginiamycin, methicillin, metronidazole, ampicillin, spectinomycin, sulfamethoxazole, trimethoprim, cloxacillin, fusidic acid, fusafungine, limecycline, gentamicin, doxycicline, carbenicillin, rifampicin, clindamycin, cephalexin, cefazolin, pivampicillin, tinidazole, amoxicillin, cephradine, minocycline, pristinamycin, fosfomycin, talampicillin, tobramycin, bacampicillin, ticarcillin, amikacin, azlocillin, cefadroxil, cefamandole, cefoxitin, cefuroxime, mezlocillin, pivmecillinam, cefaclor, cefmetazole, cefotaxime, cefsulodin, piperacillin, amoxicillin/clavulanic acid (co-amoxiclav), cefperazone, cefotiam, cefsulodin, latamoxef, netilmicin, apalcillin, ceftriaxone, micronomycin, cefmenoxime, ceftazidime, ceftizoxime, norfloxacin, cefonicide, cefotetan, temocillin, cefpiramide, imipenem/cilastatin, ofloxacin, mupirocin, aztreonam, cefoperazone/sulbactam, ticarcillin/clavulanic acid, ampicillin/sulbactam, cefixime, roxithromycin, sultamicillin, ciprofloxacin, rifaximin, azithromycin, cefaclor, flomoxef, isepamycin, midecamycin, rifapentine, teicoplanin, cefpodoxime, enrofloxacin, lomefloxacin, arbekacin, cefozidim, clarithromycin, cefdinir, cefetamet, cefpirome, cefprozil, ceftibufen, fleroxacin, loracarbef, piperacillin/tazobactam, rufloxacin, brodimoprim, dirithromycin, levofloxacin, nadifloxacin, panipenem/betamipron, sparfloxacin, cefepime, quinupristin-dalfopristin, linezolid, telithromycin, daptomycin, tigecycline, doripenem, telavancin are more preferred.

According to a further aspect, the present invention provides a cosmetic and/or pharmaceutical formulation comprising the above said composition and a physiologically acceptable vehicle or carrier, particularly for dermatological treatments and preferably for topical use.

Advantageously, the above formulation may be in the form of a water-in-oil emulsion, an oil-in-water emulsion, a monophasic gel, a sub-micellar monophasic gel, an aqueous monophasic solution, an alcoholic monophasic solution, a cream, a milk, a pomade, an ointment, which is deliverable by a swab dampened therewith, a spray and the like.

Substantially and surprisingly, the composition according to the present invention as taught in the embodiments described above, and thus the above said formulation as well, showed a high ability to control bacterial growth as well as a high bactericidal and microbiocidal activity against a plurality of both Gram-positive and Gram-negative, aerobic and anaerobic bacteria, in virtue of the combined presence of the active principles characterizing it, i.e. the triethyl citrate and the above peptide of sequence FAKALKALLKALKAL-NH2 (SEQ ID NO: 1), while simultaneously showing a high ability to protect skin lipids particularly against qualitative and quantitative type alterations, which ability is likely to be essentially the result of its ability to inhibit the hydrolysis of skin triglyceride molecules induced by bacterial lipases, i.e. induced by enzymes released by the bacteria themselves, i.e. both Gram-positive and Gram-negative, aerobic and anaerobic bacteria.

When the present composition includes one or more synergistic agents as described above, it is extremely advantageous, especially for specific treatments of the skin.

In this regard, it should be emphasized that a composition according to the invention, which comprises one or more synergistic agents belonging to the above said group of antibiotics, advantageously enables to control the occurrence of phenomena of bacterial resistance, whereas in absence of synergistic agents belonging to this group, the present composition has the advantage that it does not result in the occurrence of resistant bacteria, i.e. an acquired antibiotic resistance.

Further characteristics and advantages of the invention will become more apparent from an examination of the following detailed description of some preferred but not exclusive embodiments illustrated by way of non-limiting example with the aid of the accompanying drawings, in which:

DETAILED DESCRIPTION OF THE INVENTION

A composition according to the present invention comprises triethyl citrate and a peptide consisting of 15 amino acids of sequence FAKALKALLKALKAL-NH2 (SEQ ID NO: 1), wherein F is phenylalanine, A is alanine, K is lysine, and L is leucine.

The triethyl citrate is the ethyl ester of citric acid with EINECS name triethyl-2-hydroxypropane-1,2,3-tricarboxylate, CAS number 201-070-7, molecular formula $C_{12}H_{20}O_7$ and molecular weight 276.29, and it is an oily compound which is both water-soluble up to a concentration of 4.5% and lipid-soluble.

The peptide FAKALKALLKALKAL-NH2 (SEQ ID NO: 1), hereinafter also referred to as the Peptide for sake of simplicity, is known to have antimicrobial activity and, particularly, to be effective in controlling bacterial colonization in patients with acne, as described in document US 2007/0207112 which is incorporated herein by reference.

The Peptide is derived from a biocidal protein defined as a "bacterial/permeability-increasing protein", generally referred to as BPI, which forms part of the innate immune system as described in document US 2005/0148495, which is incorporated herein by reference.

The composition according to the invention, comprising triethyl citrate and the Peptide as the active ingredients, surprisingly and unexpectedly showed a high synergistic activity and, particularly, it showed a pronounced microbiocidal action and a high ability to inhibit bacterial colonization of both Gram-positive and Gram-negative, aerobic and anaerobic bacteria, while being simultaneously able to inhibit the degradation of skin triglyceride molecules induced by enzymes released by Gram-positive and Gram-negative, aerobic and anaerobic bacteria.

Among the bacteria found to be sensitive to the composition according to the present invention there are *Staphylococcus Aureus, Propionibacterium acne, Pseudomonas aeruginosa, Streptococcus pyogenes, Staphylococcus epidermis*.

Therefore, according to the invention, the present composition is apt to counteract bacterial infections of skin, mucous membranes and skin appendages, and it is apt to the treatment of pathologies in which a skin infection causes, or contributes to cause, detectable lesions on the skin, such as for example in acne, suppurative or non-suppurative hidradenitis, atopic dermatitis characterized by colonization by *Staphylococcus Aureus*, impetigo, interdigital infections, folliculitis, boils, post-traumatic infections, and burned skin infections.

According to the above, the present composition has shown to be particularly indicated for use in combination with a physiologically acceptable vehicle or carrier, and specifically with a cosmetically and/or pharmaceutically acceptable vehicle or carrier, in order to produce a cosmetic and/or pharmaceutical formulation preferably intended for topical use in dermatological treatments.

The composition according to the invention comprises triethyl citrate at a concentration in the range from 0.05 w/w % to 99.9 w/w %, more preferably from 0.5 w/w % to 45 w/w %, still more preferably from 2.5 w/w % to 15 w/w %.

The composition according to the invention comprises the peptide at a concentration in the range from 0.002 w/w % to 0.5 w/w %, more preferably from 0.010 w/w % to 0.35 w/w %, still more preferably from 0.010 w/w % to 0.125 w/w %.

The composition according to the invention may further comprise one or more synergistic agents selected from essential fatty acids including salts and esters thereof, salicylic acid including salts and esters thereof, zinc and derivatives thereof, azelaic acid, octadecenedioic acid and antibiotics as previously mentioned.

The antibacterial properties of the composition according to the present invention are further illustrated in the following examples and experimental tests, which are described with reference to the accompanying drawings.

Experimental Tests

The purpose of the experimental tests was to determine —and thus demonstrate—the antimicrobial activity of a composition comprising triethyl citrate and the Peptide (a composition according to the invention).

Description of the Method

A series of sample tubes, hereinafter also referred to as samples, was prepared containing a culture broth inoculated with a test microorganism and added with an aqueous solution of the composition according to the invention to be assayed at respective scaled-down concentrations, and a positive sample containing the above said culture broth alone.

Evaluation of Antibacterial Activity

Cultures of test microorganisms were incubated at a temperature and under growth conditions optimal for the specific test microorganism selected, and for a period of time sufficient to allow the microorganisms to develop.

Then, the samples showing an effective development of the microbial population were identified by visually observing their turbidity as an indicator of growth.

In detail, the samples containing the composition according to the invention at a concentration sufficient to inhibit the bacterial growth remained clear.

In the cases in which either the nature itself of a sample prevented the sample from being visually read or it was desired to determine whether the absence of bacterial growth was caused by a microbiostatic or microbiocidal action, then grafts were carried out in appropriate agar media for confirmation.

Assay Concentrations

Samples were prepared comprising a culture broth directly obtained from the culture medium and an aqueous solution of 4.5 w/w % triethyl citrate, 0.0025 w/w % peptide and water in an amount sufficient to make 100 w/w % at scaled-down concentrations particularly including 50.00 grams, 25.00 grams and 12.50 grams of the above solution per 100 milliliters of culture broth, respectively.

Test Microbial Strains

The microbial strains used for the tests were the following:

*Propionibacterium acnes* ATCC 11827 at a concentration of $1.4 \times 10^6$ cfu/ml of medium.

*Staphylococcus Aureus* ATCC 6538 at the concentration of $3.5 \times 10^3$ cfu/ml of medium Test Culture Conditions For the *Propionibacterium acnes* culture, the liquid medium Fluid Thioglycollate Medium was used at a temperature of 37° C.±1° C. under anaerobic conditions.

For the grafts used as a confirmation of the growth in the liquid medium, the Fluid Thioglycollate Medium was used at a temperature of 37° C.±1° C. under anaerobic conditions.

For the *Staphylococcus Aureus* culture, the medium Tryptic Soy Broth was used at 37° C.±1° C. with 24 hours of incubation under aerobic conditions.

For the grafts used as a confirmation of the growth in the agar medium, the medium Tryptic Soy Agar was used and Petri dishes were incubated at 37° C.±1° C. under aerobic conditions.

Evaluation of the Absence of Anaerobic Bacteria in One Gram of the Solution Containing the Active Ingredients to be Diluted with the Culture Broth The absence of anaerobic bacteria in one gram of the above solution containing the active ingredients was verified by seeding in Fluid Thioglycollate Medium and incubation at 37° C.+/−1° C. under anaerobic conditions for 72 hours.

Furthermore, the absence of mesophilic aerobic microorganisms in 1 gram of the same solution containing the active ingredients as above was verified by seeding in Tryptic Soy Broth and incubation at 37° C.±1° C. for 48 hours.

Positive Controls

Fertility of the medium and viability of the microorganisms: For both the microbial strains indicated above, tests were carried out with both the medium and the microorganisms but in the absence of the aqueous solution comprising the composition according to the invention, under the same culture conditions used in the experimentation as described above.

Sterility of the Medium and Verification of the Aseptic Conditions

For both the culture media used for the incubation, tests were carried out in the absence of both the aqueous solution comprising the composition according to the invention and the microorganisms, under the conditions used in the experimentation as described above.

Test Results for *Propionibacterium acnes*

Results obtained from visual observation in duplicate:

The results are obtained by visually reading the microbial growth in the afore said samples (sample tubes) as prepared above, which were evaluated based on the turbidity of the culture medium after about 72 hours of incubation.

Figure 3A:
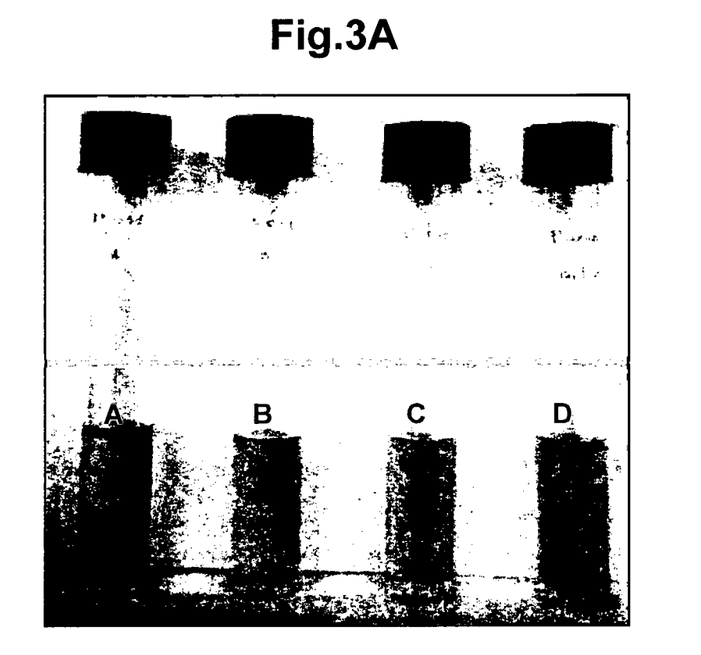
FIGS. 3A and 3B are pictures each showing four samples, three containing an aqueous solution comprising different concentrations of a composition according to the present invention including triethyl citrate and the peptide FAKA-LKALLKALKAL-NH2 (SEQ ID NO: 1), as well as a culture broth comprising the test microorganism *Propionibacterium acnes* ATCC 11827, the fourth sample being a positive control consisting of the above said culture broth alone.
Figure 3B:
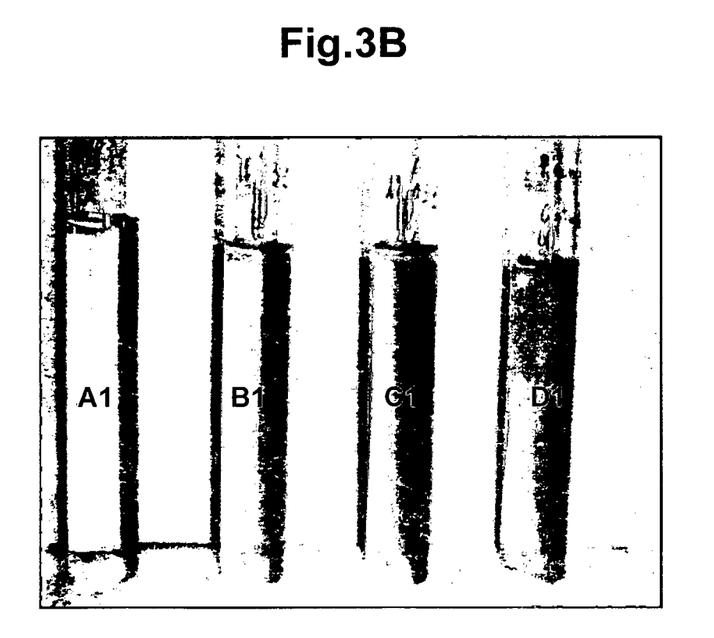

The results, which were evaluated in duplicate as stated above, are illustrated in the examples of FIGS. 3A and 3B, in which A, B and C and A1, B1 e C1, respectively, denote the above samples at the respective scaled-down concentrations as reported above (50, 25, and 12.5 w/w %).

From the above said figures, it can be noted that all the samples comprising the aqueous solution based on the composition according to the invention, although at various concentrations, were clear and transparent, in contrast to the positive control, represented by the fourth sample D and D1, respectively, in which a positive growth is observed in both the sample tubes containing the medium Fluid Thioglycollate Medium with *Propionibacterium acnes*.

The results obtained from this reading were verified by carrying out subsequent grafts in the liquid medium after about 72 hours of incubation.

Table 1 shows, for each sample concentration rounded to two decimal places, the results for the grafts at the same concentration.

TABLE 1

|  | A | B | C |
| --- | --- | --- | --- |
| Sample concentration | 50.00% | 25.00% | 12.50% |
| Growth in agar medium | No growth | No growth | No growth |

Sterility of the Medium and Verification of the Aseptic Conditions

Absence of growth.

Results of the Test for *Staphylococcus Aureus*

Results of the visual observation:

The results relate to the visual reading of microbial growth in the afore said samples (sample tubes) as prepared above, which were evaluated based on the turbidity of the culture medium after about 24 hours of incubation.

Figure 4:
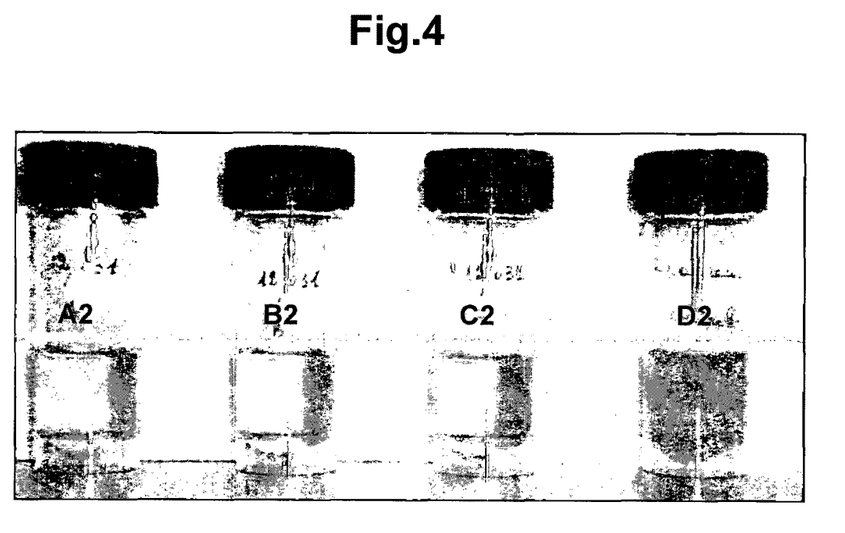
FIG. 4 is a picture showing four samples, three containing an aqueous solution comprising different concentrations of a composition according to the present invention including triethyl citrate and the peptide FAKALKALLKALKAL-NH2 (SEQ ID NO: 1), as well as a culture broth comprising the test microorganism *Staphylococcus Aureus* ATCC 6538, the fourth sample being a positive control consisting of the above said culture broth alone.
Figure 5:
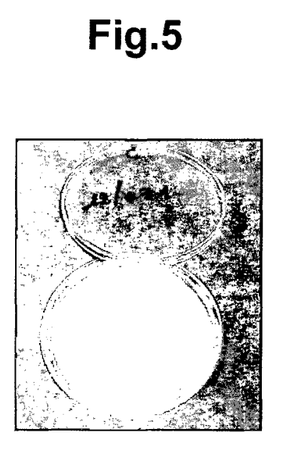
FIG. 5 is a picture showing the absence of growth of the test microorganism in a plate seeded with a graft of the sample of FIG. 4 at the lowest concentration of the composition according to the invention.

The results are illustrated in the example of FIG. 4, in which A2, B2 and C2 denote the afore said samples at scaled-down concentrations which are clear and transparent, in contrast to the positive control sample containing the medium Tryptic Soy Broth with *Staphylococcus Aureus*—denoted as D2—which showed a positive growth.

The results obtained from this reading were verified by carrying out subsequent grafts in the solid medium after about 24 hours of incubation.

Figure 6:
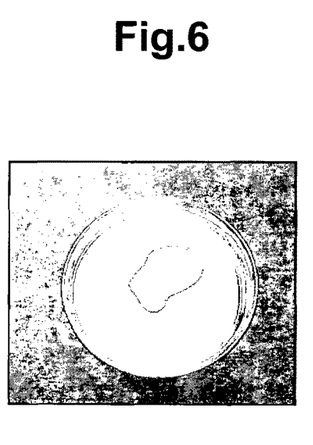
FIG. 6 is a picture showing the proliferation of the test microorganism in a plate seeded with a graft of the positive control sample of FIG. 4.
Figure 7:
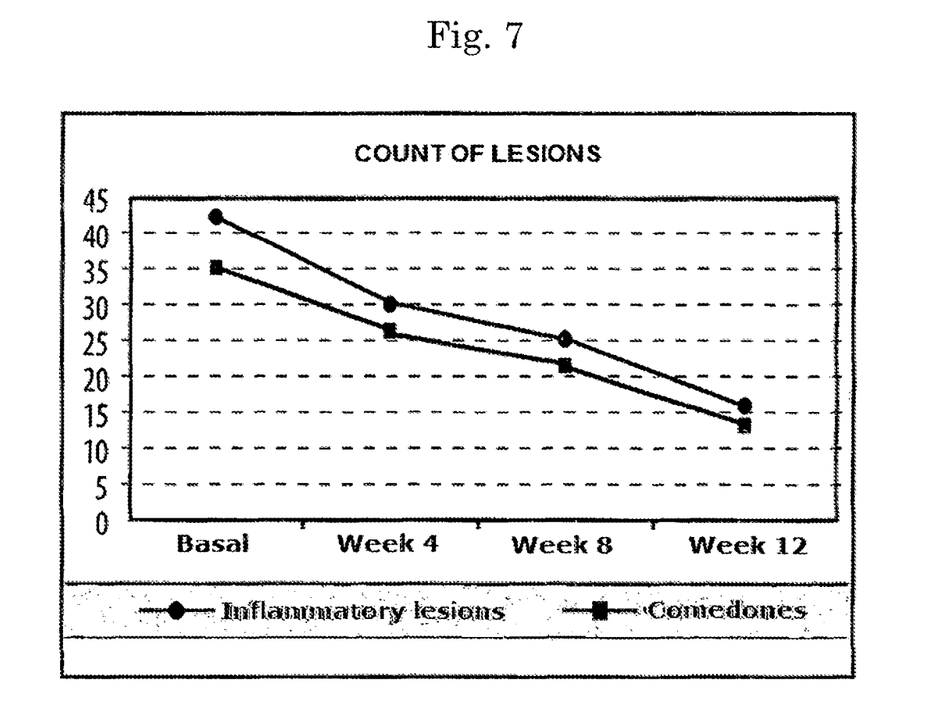
FIG. 7 illustrates a graph for inflammatory and comedonal acne, respectively, showing the number of visible lesions on skin samples as a function of time, particularly before a treatment with a composition according to the present invention (basal state) and at different time intervals throughout a treatment with a composition according to the present invention.

The examples of FIGS. 6 and 7 show and highlight the absence of bacterial growth in a Tryptic Soy agar plate seeded with a graft at the lowest assayed concentration (12.50%) of the sample, respectively, as compared to a graft with the positive control sample in which a bacterial growth is observed.

Table 2 shows, for each sample concentration rounded to two decimal places as indicated above, the final results for the grafts obtained at the same assayed concentration.

TABLE 2

|  | A | B | C |
| --- | --- | --- | --- |
| Sample concentration | 50.00% | 25.00% | 12.50% |
| Growth in agar medium | No growth | No growth | No growth |

Sterility of the Medium and Verification of the Aseptic Conditions

Absence of growth.

From the above it can be stated that the composition according to the invention, specifically a composition consisting of triethyl citrate (4.5 w/w %) and the Peptide (0.025 w/w %), showed an excellent antimicrobial activity against both the assayed organisms.

In fact, it has to be pointed out that none of the assayed samples, at the respective concentration, allowed microbes to growth.

Furthermore, it has to be highlighted that, according to the same methods as described above, a composition based on triethyl citrate, i.e. triethyl citrate alone at a concentration of 4.5 w/w % in water q.s. to 100 w/w % without the Peptide, showed a very mild microbiocidal activity (25% survival of the bacterial population) in contrast to a total inhibition of the living bacteria with the composition according to the invention.

Evaluation of the efficacy and tolerability of the treatment of a comedonal and inflammatory acne localized to the areas of chest and back with the use of an oil-in-water emulsion comprising a composition according to the invention obtained as follows:

| No. | Description | weight % |
| --- | --- | --- |
| Phase A) | | |
| 01 | Cetearyl glucoside | 4.2% |
| 02 | Butylated hydroxytoluene | 0.01% |
| 03 | Ethyl linoleate | 3.0% |
| 04 | Salicylic acid | 0.5% |
| 05 | Triethyl citrate | 9% |
| Phase B) | | |
| 06 | Peptide | 0.0025% |
| 07 | Demineralized water | 5.0% |

-continued

| No. | Description | weight % |
|---|---|---|
| Phase C) | | |
| 08 | Propylene glycol | 1.5% |
| 09 | Phenoxyethanol | 0.8% |
| 10 | Methylparaben sodium salt | 0.25% |
| 11 | Zinc lactate | 1.25% |
| 12 | Water | q.s. to 100% |

Method of Preparation:

Step A): mix 01+02+03+04+05 and heat to 75° C.;

Step B): dissolve 06 in 07;

Step C): dissolve 10 +11 in 12; mix 08+09 with the resulting solution and heat up to 75° C.

When at the temperature of 75° C., combine Phase A) with Phase C). Leave to stir while deaerating and, when at the temperature of 35° C., add Phase B).

The efficacy and tolerability of the emulsion comprising the composition according to the invention as indicated above, in the treatment of an inflammatory and comedonal acne localized to back and neckline, were studied.

Patient enrollment: 12 patients aged between 13 and 22 years and suffering from a mild-moderate grade acne on the back and/or neckline.

Study design: Open-label study.

Application of the emulsion (lotion): twice a day for 12 weeks.

Follow-up: 4, 8 and 12 weeks.

Evaluation: Count of lesions on the reference area. Picture evaluation.

Patients after 12 weeks of treatment: 12

Result according to the investigator: the emulsion was effective.

Figure 1:
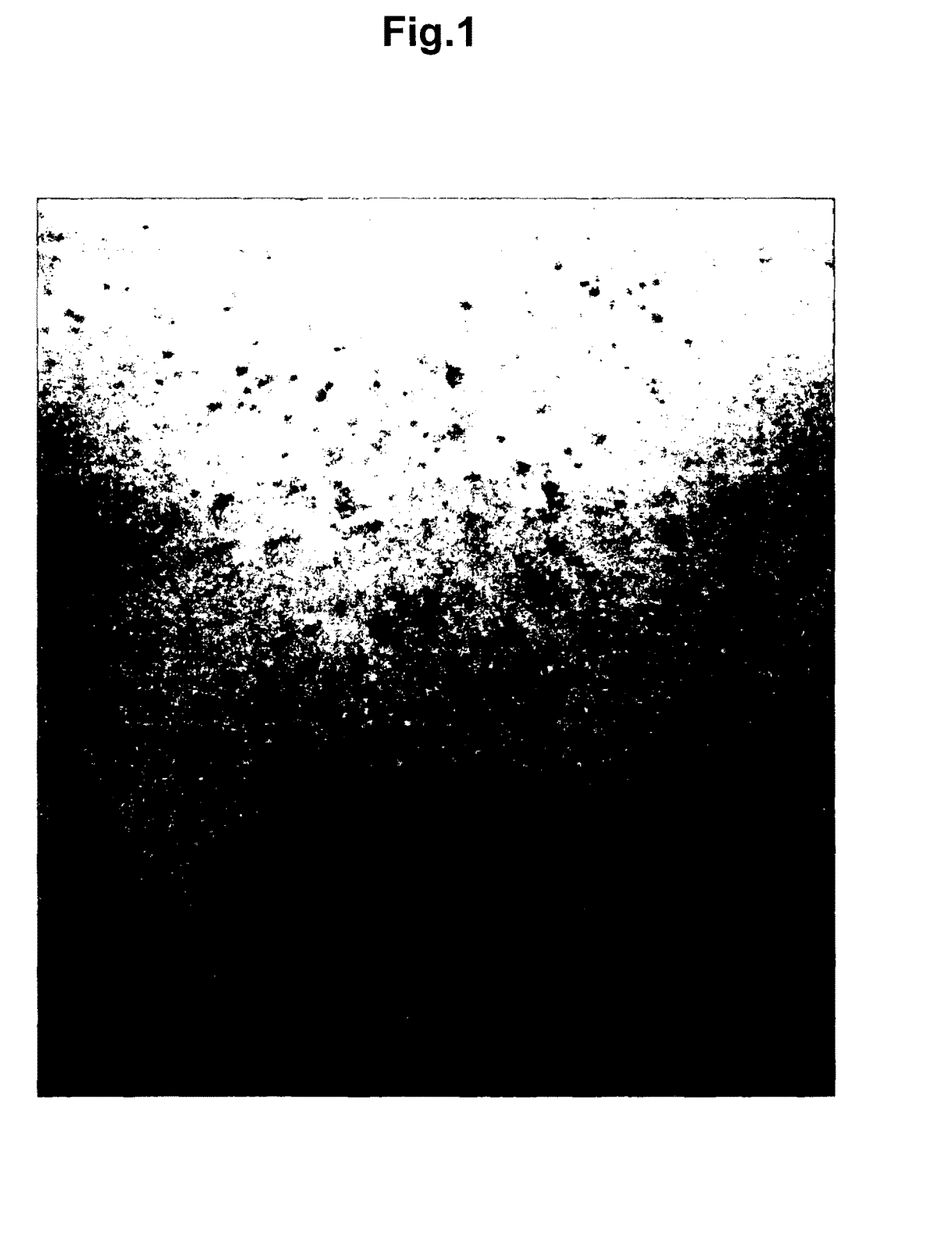
FIG. 1 is a picture of a skin portion, particularly the dorsal area, of a subject suffering from a moderate-grade comedonal and inflammatory acne before a treatment with a composition according to the present invention.
Figure 2:
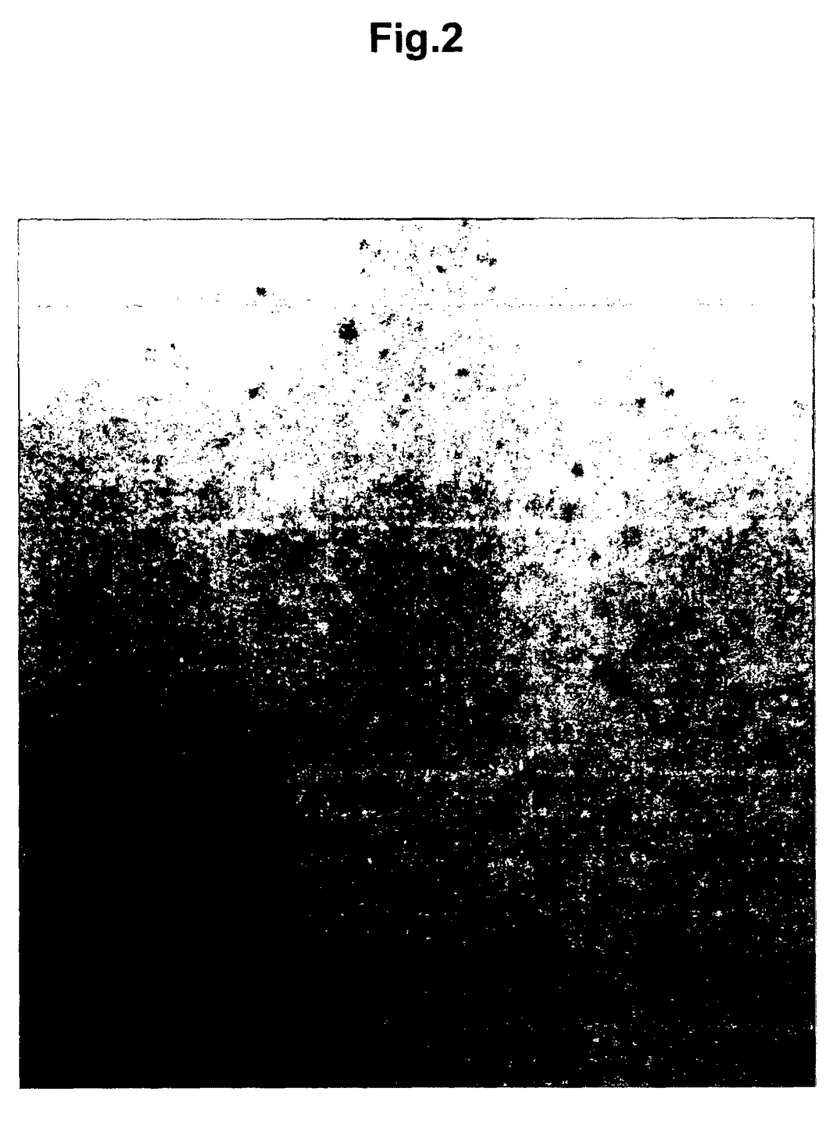
FIG. 2 is a picture of the skin portion of FIG. 1 after a 12-weeks treatment with the composition according to the present invention.

Result according to the patients: the emulsion was effective:

Evaluation according to the patients after treatment: good, patients were satisfied Tolerability: excellent Observed side effects: none The example of FIG. 7 graphically illustrates the data of the above described test, whereas the examples of FIGS. 1 and 2 illustrate a sample of skin from one of the 12 enrolled patients before and after the above described treatment, respectively.

Further examples of cosmetic and/or pharmaceutical preparations or formulations comprising a composition according to the invention, along with the preparation and use thereof, are given below:

| PREPARATION 1 - hydroalcoholic monophasic solution for the treatment of acne ||||
| No. | Description | weight % |
|---|---|---|
| 01 | Triethyl citrate | 10% |
| 02 | Peptide | 0.01% |
| 03 | Ethyl alcohol | 45.0% |
| 04 | Water | q.s. to 100% |

Method of preparation: dissolve 02 in 03; add 01 to the resulting solution, make up the volume to 100 with 04 under stirring

| PREPARATION 2 - monophasic gel for the treatment of acne ||||
| No. | Description | weight % |
|---|---|---|
| 01 | Triethyl citrate | 4.5% |
| 02 | Peptide | 0.0025% |
| 03 | Carbomer | 1.0% |
| 04 | Sodium hydroxide | q.s. to pH 6 |
| 05 | Demineralized water | q.s. to 100.00% |

Method of preparation: mix 01 with 05, dissolve 02 in the resulting solution; disperse 03 in the resulting solution; neutralize with 04. The whole operation is to be carried out under stirring.

| PREPARATION 3 - oil-in-water emulsion for the treatment of atopic dermatitis ||||
| No. | Description | weight % |
|---|---|---|
| Phase A) | | |
| 01 | Steareth 2 | 3.0% |
| 02 | Steareth 21 | 2.0% |
| 03 | PPG-15 stearyl ether | 8.0% |
| 04 | Butylated hydroxytoluene | 0.01% |
| 05 | Triethyl citrate | 10.0% |
| 06 | Ceramide IV | 0.005% |
| Phase B) | | |
| 07 | Peptide | 0.0025% |
| 08 | Demineralized water | 5.0% |
| Phase C) | | |
| 09 | Propylene glycol | 1.5% |
| 10 | Phenoxyethanol | 0.8% |
| 11 | Methylparaben sodium salt | 0.25% |
| 12 | Water | q.s. to 100% |

Method of preparation: Step A): mix 01+02+03+04+05+06 and heat to +75° C.;

Step B): dissolve 07 in 08;

Step C): dissolve 11 in 12; mix 10+09 with the resulting solution, and heat up to 75° C.

When at the temperature of 75° C., combine Phase A) with Phase C). Leave to stir while deaerating and, when at the temperature of 35° C., add Phase B).

| PREPARATION 4 - alcoholic solution for the treatment of suppurative hidradenitis ||||
| No. | Description | weight % |
|---|---|---|
| 01 | Triethyl citrate | 40.0% |
| 02 | Peptide | 0.01% |
| 03 | Ethyl alcohol | q.s. to 100.0% |

Method of preparation: dissolve 02 in 03; mix 01 with the resulting solution.

| PREPARATION 5 - antibacterial solution ||||
| No. | Description | weight % |
|---|---|---|
| 01 | Triethyl citrate | 4.5% |
| 02 | Peptide | 0.0025% |
| 03 | Demineralized water | q.s. to 100.0% |

Method of preparation: dissolve 02 in 03; mix 01 with the resulting solution.

| PREPARATION 6 - antibacterial and anti-acne solution | | |
|---|---|---|
| No. | Description | weight % |
| 01 | Triethyl citrate | 4.5% |
| 02 | Peptide | 0.0025% |
| 03 | Clindamycin | 1% |
| 04 | Ethyl alcohol | q.s. to 100.0% |

Method of preparation: dissolve 02+03 in 04; mix 01 with the resulting solution.

| PREPARATION 7 - antibacterial and anti-acne solution | | |
|---|---|---|
| No. | Description | weight % |
| 01 | Triethyl citrate | 4.5% |
| 02 | Peptide | 0.0025% |
| 03 | Erythromycin | 1.5% |
| 03 | Ethyl alcohol | q.s. to 100.0% |

Method of preparation: dissolve 02+03 in 04; mix 01 with the resulting solution.

The advantages of the present invention, which already appeared clear throughout the above description, may be summarized by pointing out that there is provided an antibacterial composition comprising triethyl citrate and the Peptide as the active ingredients as described above, which has high efficacy against both aerobic and anaerobic, Gram-positive and Gram-negative bacteria, while being simultaneously able to protect skin lipids against qualitative and quantitative alterations due to its ability to inhibit the hydrolysis of skin triglyceride molecules induced by bacterial lipases.

Therefore, advantageously, the present composition combines an effective bactericidal and microbiocidal action with an effective protective action on skin and mucous membranes, thereby ensuring the maintenance of their natural characteristics.

Again, the present composition was found to be free from side effects or otherwise unwanted effects, and it showed an excellent tolerability.

Accordingly, the present composition is advantageously indicated for the treatment of bacterial lesions of skin, mucous membranes and skin appendages, and for the treatment of pathologies in which a skin infection causes, or contributes to cause, detectable lesions on the skin, such as for example in acne, suppurative or non-suppurative hidradenitis, atopic dermatitis characterized by colonization by *Staphylococcus Aureus*, impetigo, interdigital infections, folliculitis, boils, post-traumatic infections, and burned skin infections.

A person skilled in the art may make various changes to the present invention, in its illustrated and described embodiments, to satisfy contingent and specific requirements, on the other hand all contained in the scope of protection of the invention as defined in the following claims.

The invention claimed is:

1. An antibacterial composition comprising triethyl citrate and a peptide consisting of 15 amino acids of sequence FAKALKALLKALKAL-NH2 (SEQ ID NO: 1), wherein F is phenylalanine, A is alanine, K is lysine, and L is leucine.

2. The composition according to claim 1, comprising triethyl citrate in a concentration from 0.05% to 99.9% w/w.

3. The composition according to claim 1, comprising said peptide in a concentration from 0.002% to 0.5% w/w.

4. The composition according to claim 1, further comprising one or more synergistic agents selected from the group consisting of:
essential fatty acids, including salts and esters thereof;
salicylic acid, including salts and esters thereof;
zinc and derivatives thereof;
azelaic acid;
octadecenecloic acid and antibiotics.

5. The composition according to claim 4, wherein said one or more synergistic agents is selected from the group consisting of essential fatty acids and salts and esters thereof in a concentration from 0.01% to 50% w/w, or from 0.5% w/w to 15% w/w, or a combination thereof.

6. The composition according to claim 4 wherein said one or more synergistic agents is selected from the group consisting of salicylic acid and salts and esters thereof in a concentration from 0.2% w/w to 15% w/w, or from 0.5% w/w to 2% w/w or a combination thereof.

7. The composition according to claim 4, wherein said one or more synergistic agents is selected from the group consisting of zinc and derivatives thereof in a concentration from 0.2% w/w to 5% w/w, or from 0.5% w/w to 2% w/w, or a combination thereof.

8. The composition according to claim 4, wherein said one or more synergistic agents is selected from the group consisting of azelaic acid and octadecenedioic acid in a concentration from 1% w/w to 65% w/w, or from 2% w/w to 15% w/w.

9. The composition according to claim 4, wherein said one or more synergistic agents is selected from the group consisting of antibiotics in a concentration from 0.1% w/w to 5% w/w, or from 0.5% w/w to 2% w/w, or a combination thereof.

10. An antibacterial composition according to claim 1, for topical use on injured or healthy skin and mucous membranes, including oral mucosa and skin appendages, for the treatment of acne, suppurative or non-suppurative hidradenitis, atopic dermatitis accompanied by colonization from Staphylococcus Aureus, impetigo, interdigital infections, folliculitis, boils, posttraumatic infections, and burned skin infections.

11. A cosmetic and/or pharmaceutical formulation comprising a composition according to claim 1, and a physiologically acceptable carrier.

12. The composition according to claim 4, wherein said one or more synergistic agents is selected from the group consisting of linoleic acid, linolenic acid and oleic acid, or a combination thereof.

13. The composition according to claim 12, wherein said one or more synergistic agent is in a concentration from 0.01% to 50% w/w, or from 0.5% w/w to 15% w/w or a combination thereof.

14. The composition according to claim 4, wherein said one or more synergistic agents is selected from the group consisting of zinc oxide, zinc sulfate, zinc pyrithione, zinc mandelate, zinc acetate, zinc glycolate, zinc salicylate, zinc lactate, zinc pyruvate, or a combination thereof.

15. The composition according to claim 14, wherein said one or more synergistic agents is in a concentration from 0.2% w/w to 5% w/w, or from 0.5% w/w to 2% w/w, or a combination thereof.

16. The composition according to claim 4, wherein said one or more synergistic agents is selected from the group consisting of isoxacillins including oxacillin, cloxacicillin, dicloxacillin, nafcillin and flucloxacillin; aminopenicillins including ampicillin and amoxicillin; carboxypenicillins including carbenicillin and ticarcillin; ureidopenicillins including mezlocillin, piperacillin, azlocillin and apalcillin; benzylpenicillin, sulfaclimidine, sulfamerazine, streptomycin, sulfadiazine, chlortetracycline, chloramphenicol, neomycin, oxytetracycline, penicillin G procaine, erythromycin, benzathine penicillin, spiramycin, tetracycline, thiamphenicol, vancomycin, phenoxymethylpenicillin, colistin, demeclocycline, virginiamycin, methicillin, metronidazole, ampicillin, spectinomycin, sulfamethoxazole, trimethoprim, cloxacillin, fusidic acid, fusafungine, limecycline, gentamicin, doxycicline, carbenicillin, rifampicin, clindamycin, cephalexin, cefazolin, pivampicillin, tinidazole, amoxicillin, cephradine, minocycline, pristinamycin, fosfomycin, talampicillin, tobramycin, bacampicillin, ticarcillin, amikacin, azlocillin, cefadroxil, cefamandole, cefoxitin, cefuroxime, mezlocillin, pivmecillinam, cefaclor, cefmetazole, cefotaxime, cefsulodin, piperacillin, amoxicillin/clavulanic acid (co-amoxiclav), cefperazone, cefotiam, cefsuloclin, latamoxef, netilmicin, apalcillin, ceftriaxone, micronomycin, cefmenoxime, ceftaziclime, ceftizoxime, norfloxacin, cefonicide, cefotetan, temocillin, cefpiramide, imipenem/cilastatin, ofloxacin, mupirocin, aztreonam, cefoperazone/sulbactam, ticarcillin/clavulanic acid, ampicillin/sulbactam, cefixime, roxithromycin, sultamicillin, ciprofloxacin, rifaximin, azithromycin, cefaclor, flomoxef, isepamycin, midecamycin, rifapentine, teicoplanin, cefpodoxime, enrofloxacin, lome'floxacin, arbekacin, cefoziclim, clarithromycin, cefllinir, cefetamet, cefpirome, cefprozil, ceftibufen, fleroxacin, loracarbef, piperacillin/tazobactam, rufloxacin, brodimoprim, dirithromycin, levofloxacin, nadifloxacin, panipenem/betamipron, sparfloxacin, cefepime, quinupristin-dalfopristin, linezolid, telithromycin, daptomycin, tigecycline, doripenem, telavancin, or a combination thereof.

17. The composition according to claim 16, wherein said one or more synergistic agents is in a concentration from 0.1% w/w to 5% w/w, or from 0.5% w/w to 2% w/w, or a combination thereof.

\* \* \* \* \*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Composizione antibatterica per uso topico

<400> SEQUENCE: 1

Phe Ala Lys Ala Leu Lys Ala Leu Leu Lys Ala Leu Lys Ala Leu
1               5                   10                  15